United States Patent [19]

Olsson et al.

[11] Patent Number: 5,471,977
[45] Date of Patent: Dec. 5, 1995

[54] METHOD AND APPARATUS FOR THE CONTROL AND INDEPENDENT MONITORING OF AN EXTREMELY SMALL GAS FLOW

[75] Inventors: Sven-Gunnar Olsson, Arloev; Goergan Rydgren, Bunkeflostrand; Anders Larsson, Kaevlinge, all of Sweden

[73] Assignee: Siemens Aktiengesellschaft, Munich, Germany

[21] Appl. No.: 066,182

[22] Filed: May 21, 1993

[30]  Foreign Application Priority Data

May 21, 1992 [EP] European Pat. Off. .............. 92108636

[51] Int. Cl.[6] ............................. A61M 16/00; A62B 7/00; A62B 9/00; F16K 31/02
[52] U.S. Cl. ................................ 128/204.22; 128/204.21; 128/205.23
[58] Field of Search ......................... 128/203.12, 203.25, 128/204.18, 204.22, 204.25, 204.29, 205.11, 205.23, 205.28, 205.24, 204.21

[56]  References Cited

U.S. PATENT DOCUMENTS

| 4,191,952 | 3/1980 | Schreiber et al. | 128/203.25 |
|---|---|---|---|
| 4,215,409 | 7/1980 | Strowe | 128/204.22 |
| 4,241,732 | 12/1980 | Berndtsson | 128/204.21 |
| 4,328,823 | 5/1982 | Schreiber | 137/88 |
| 4,380,233 | 4/1983 | Caillot | 128/204.21 |
| 4,905,685 | 3/1990 | Olsson et al. | 128/204.21 |
| 4,928,684 | 5/1990 | Breitenfelder | 128/204.21 |

FOREIGN PATENT DOCUMENTS

| 0039932A2 | 5/1981 | European Pat. Off. | ........ A61M 17/00 |
|---|---|---|---|
| 0032349A1 | 7/1981 | European Pat. Off. | ........ A61M 16/00 |
| 2548549A1 | 1/1985 | European Pat. Off. | .......... B01F 5/10 |
| 2053512 | 2/1981 | United Kingdom | ........... G05B 15/02 |
| 2176313 | 12/1986 | United Kingdom | ........... G05D 11/10 |

OTHER PUBLICATIONS

Siemens AG Brochure entitled "The innovative solution for advanced ventilatory treatment" Servo Ventilator 300.

*Primary Examiner*—Kimberly L. Asher
*Attorney, Agent, or Firm*—Hill, Steadman & Simpson

[57]  ABSTRACT

A method and apparatus for independent monitoring of a flow-through quantity and, potentially, of a concentration of a gas flow that is extremely small in comparison to a respiratory gas flow is provided. The valve for the control of this small gas flow can not be controlled via the overall gas flow. In order to be able to simply and reliably monitor the flow-through quantity and the concentration of this small gas flow without a gas analyzer and independently of gas flow regulators that are usually present, it is provided that the small gas flow be separately measured and compared to a value derived from the respiratory gas flow. Given the presence of prescribable criteria, an alarm is triggered and the flow-through quantity of the small gas flow is, for example, interrupted.

4 Claims, 2 Drawing Sheets

METHOD AND APPARATUS FOR THE CONTROL AND INDEPENDENT MONITORING OF AN EXTREMELY SMALL GAS FLOW

BACKGROUND OF THE INVENTION

The invention is directed to a method and to an apparatus for the independent monitoring of the flow-through quantity and, potentially, of the concentration of a further gas which is added to a respiratory gas in relatively small concentrations.

In the ventilator-controlled or ventilator-enhanced respiration of humans or animals, it can be advantageous, for example given low lung capacity, to add an extremely low concentration of a further gas to the respiratory gas. For example, it has thus been shown that an admixture of nitrogen oxide (NO) in a concentration of 10–100 ppm promotes the blood supply of the alveolae and the lungs.

Further, it can also be desirable to add a gas that does not participate in the gas exchange, such as $SF_6$, in similarly low concentrations in order, for example, to be able to measure the lung volume with the assistance of this gas. These are only two examples of how it can be desirable under certain circumstances to add an extremely low concentration of an additional gas to the respiratory gas, whereby respiratory gas, in the broadest sense, is intended to cover all gases or gas mixtures here that are employed in respirator treatment or narcosis.

Particularly given the admixture of nitrogen oxide (NO), it must be considered that even small concentrations of this gas are toxic and that the concentration on the order of magnitude of 10–100 ppm must be carefully monitored. Moreover, nitrogen oxide in higher concentrations is unstable together with $O_2$ and therefore can only stably exist highly diluted, for example as a 1% solution in nitrogen gas. Even given a desired concentration of the nitrogen oxide of 100 ppm and a dilution of 1% in nitrogen gas, the nitrogen oxide/nitrogen gas mixture to be mixed in only amounts to 1% of the remaining respiration gas. The corresponding gas flow lies within standard margins of error for the controlled gas flow of the respiration gas and is practically negligible in comparison thereto.

The concentration for some auxiliary gases could be identified with the assistance of an additional gas analyzer; this, however, would represent considerable added expense.

SUMMARY OF THE INVENTION

An object of the invention is to be able to simply and reliably monitor the flow-through quantity and the gas concentration of the further gas without a gas analyzer and independently of gas flow controls that are usually present. A further object of the invention is in making this monitoring independent of the further gas employed. A further object of the invention is to further enhance the safety for the living being ventilated with such a further gas.

With the present invention, an independent monitoring of the flow-through quantity, and potentially concentration, of a further gas to a respiratory path of a human or animal is provided. The gas flow of the further gas is small in comparison to the gas flow of a respiratory gas being delivered. The independently measured gas flow of the further gas is compared to a measured respiratory gas flow and, given presence of prescribable criteria, an alarm is triggered or the flow-through quantity of the further gas is influenced.

The invention thereby departs on the basis of the fundamental concept of a known ventilator, for example the servo ventilator 300 as fundamentally described in the brochure "The Innovative Solution for Progressive Respirator Therapy", 1991. This ventilator contains a separate gas module for every gas, the gas flow for every gas being capable of being controlled with high precision and extremely short response time with the assistance thereof. The valve contained in every module comprising pressure gauge, flow meter and electronic control is disclosed, for example, in European Patent Application 90120843.9, incorporated herein. One module, for example, can be employed for the delivery of air; and a further module can be employed for the delivery of pure oxygen. The gas flow in every module is determined via a flow meter and is utilized for the control of the valve in order to assure the rated flow adjustable at the ventilator. In addition, the servo ventilator 300 contains a further flow meter in the expiration line in order to measure the expirational gas flow. This expirational gas flow meter can be utilized for monitoring the overall flow that is set by the inspiratorial gas valves. When the signals that the flow meters of the individual modules generate are added up, then the sum of these signals corresponds to the overall flow and, given the assumption that no leaks are present, should correspond to the expirational flow, averaged, for example, over a breadth.

A further module can be provided for the delivery of a further gas such as, for example, nitrogen oxide. It is necessary under certain circumstances to modify the valve for the further gas in order to thus be able to control small gas quantities with adequate precision at all. For example, it can be necessary to reduce the size of the valve opening and to vary the range of measurement of the flow meter. This valve is also provided with its own gas flow meter. Since the gas flow generated by this valve, however, is negligible in comparison to the respiratory gas flow, a monitoring of this valve and of the gas flow produced therewith is not possible via the total expirational gas flow. Even when it is initially assumed that the servo control of this valve generates the desired and set gas flow with adequate precision, one cannot rely only thereon in unrestricted fashion for safety reasons. According to the invention, an independent monitoring of the gas concentration of the further gas is therefore provided. For this purpose, the further gas flow is measured a second time via an additional flow meter, which is advantageously directly arranged following the output of the corresponding control valve, potentially with an adapted range of measurement. The output signal of this flow meter, however, is now not compared to the rated value for the flow to be set, but to a signal that is derived from the signal of the first flow meter. For example, the signal of the additional flow meter, and thus the gas flow of the further gas, is compared to the respiratory gas flow actually achieved, whereby the respiratory gas flow value is reduced by a factor by which the further gas flow should be smaller. When, for example, it is provided that the further gas flow should correspond to 1% of the respiratory gas flow, the output signal of the first flow meter is diminished by the factor 100, or the output signal of the additional flow meter is increased by the factor 100. Alternatively, the range of measurement of the further and/or additional flow meter can be correspondingly changed. The signals are subsequently compared. Given a deviation above a prescribable value, an alarm is triggered, or the flow-through quantity of the further gas is influenced. In a further development of the invention, the delivery of the further gas is stopped, i.e. the further valve is closed. When the respiratory gas is composed of a plurality of constituents, for example air and oxygen, the sum of both flow meters is employed as a comparison value.

In the delivery of nitrogen oxide, in order to prevent $NO_2$ from forming in the respiratory gas under the influence of the oxygen, the mixing of the further gas to the respiratory gas should occur as close as possible to the patient, or even in the patient's respiratory paths. A concentration measurement in the gas mixture thereby becomes practically impossible. As a result of the, method of the invention and the corresponding apparatus, however, the identification of the concentration and monitoring are advantageously possible. It is provided in a further development of the invention that the rated value for the control of the first valve, and thus for the control of the respiratory gas flows, is also connected onto a first potentiometer, and the signal adjustably taken from this potentiometer forms the dated value for the further valve. The rated value for the further valve is thus formed in that the rated value for the overall flow is passively voltage-divided. This thereby involves a matter of a hardware solution. Within the framework of the invention, it is likewise possible to implement the derivation of the rated value for the further valve from the rated value for the overall gas flow in terms of software.

An especially advantageous and simple development of the invention results when a double potentiometer is provided, whereby the one potentiometer, as already set forth, serves the purpose of setting the rated value for the further valve and the output signal of the flow meter or flow meters for the respiratory gas is connected onto the other potentiometer, and that the signal taken thereat identically as at the first potentiometer represents the signal derived from the respiratory gas flow, and thus a comparison quantity for the independent monitoring of the concentration of the further gas.

It is structurally advantageous to arrange the additional flow meter directly at the output of the further valve. Chronological delays with which changes of the gas flow propagate in lines are thereby kept optimally low. There is thus the possibility of constantly comparing the gas flow of the further valve to the gas flow of the respiratory gas, and thus of constantly monitoring the concentration. Since, however, chronological delay and brief-duration fluctuations cannot be entirely precluded here, it is provided in a development of the invention to separately integrate both signals via an integrator, and to thus average out chronological fluctuations. The output signals of the integrators can be compared to one another via a comparator or, advantageously, via two comparators, whereby the signal derived from the actual value of a respiratory gas flow, for example, is amplified such that it represents an upper and lower limit value for the allowable concentration; and that one limit value forms the comparison value in one comparator and the other limit value forms the comparison value in the other comparator.

In addition to triggering the alarm, of course, the possibility is also established here, given an upper crossing of the limit values, for example, completely closing the further valve in order, in particular, to prevent an excessively high concentration of gas, such as nitrogen oxide.

DESCRIPTION OF THE PREFERRED EMBODIMENTS

Figure 1:
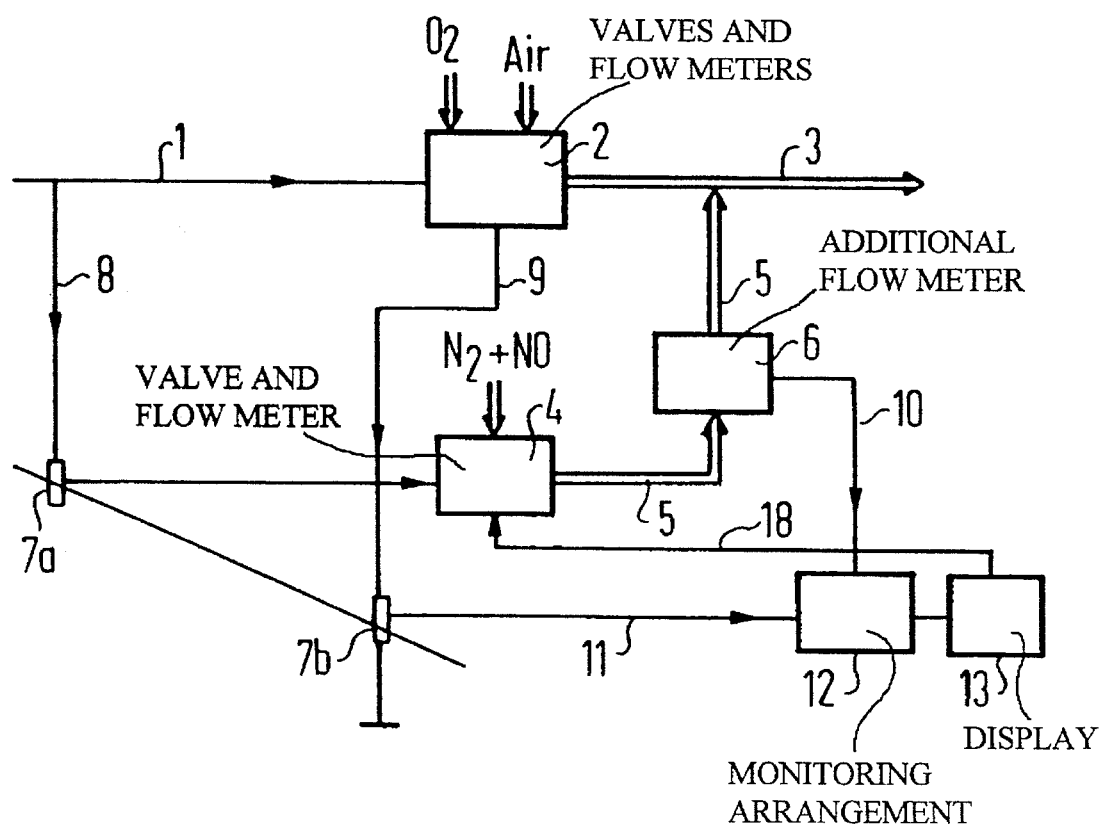
FIG. 1 is a schematic illustration of an apparatus for monitoring the flow-through quantity of the further gas having a low gas flow.

FIG. 1 shows a block circuit diagram for control of the respiratory gas flow, of the further gas flow, as well as the independent, additional monitoring of the further gas flow. A rated value for the respiratory gets flow is forwarded via a line 1 onto the valve or valves 2 for controlling the respiratory gas flow. It is assumed in the present embodiment that the respiratory gas is composed of air and oxygen, each of which is respectively controlled via a separate valve. The respiratory gas flow delivered by both valves 2 is supplied via a common line 3 to a patient (not shown). Further, a valve 4 is for the control of the further gas, in this case a gas mixture of, for example, 1% NO and 99% $N_2$. The gas flow controlled by the further valve 4 is supplied via a line 5 to the line 3 leading to the patient. Although not shown in the schematic block diagram, all valves 2, 4 are provided with a flow meter via which the generated flow can be identified. An additional flow meter 6 is provided in the line 5 from the further valve 4 to the patient line 3. Moreover, a double potentiometer 7a, 7b is provided via which the rated value for the further valve 4 for controlling the concentration of nitrogen oxide and for generating a rated value for monitoring this concentration can be taken. For this purpose, the rated value for the respiratory gas flow is connected onto tile potentiometer 7a via a line 8; this rated value, for example, can be taken from the line 1. The output signal of the flow meter (not shown) allocated to the valve 2 is connected onto the potentiometer 7b via a line 9. When the respiratory gas is composed of air and oxygen, and when both are controlled via separate valves, then the signal on the; line 9 represents the sum of the two signals coming from the two flow meters.

It is also provided that the signal of the further flow meter is amplified by a prescribable factor (100 in this case) before it is utilized for regulating the gas flow of the further gas. Instead of this amplification, the range of measurement of the further flow meter can also be correspondingly changed. This means that the gas flow regulated by this valve amounts to a maximum of 1% of the respiratory gas flow when the double potentiometer 7a, 7b is set such that the rated value that is taken corresponds to the original rated value. Given a different setting of the potentiometer 7a, 7b, the gas flow controlled by the further valve amounts to only a fraction of a percent.

When, as in this example, a low concentration of nitrogen oxide is to be mixed to the respiratory gas, and this concentration should remain on the order of magnitude between 10 and 100 ppm, and when, beyond this, the nitrogen oxide is only stable in a greater dilution in nitrogen gas so that a mixture of 1% nitrogen oxide and 99% nitrogen gas is selected, then a respiratory gas flow through the further valve 4 of 1% of the total respiratory gas flow corresponds to a concentration of 100 ppm nitrogen oxide. When a lower voltage is taken via the potentiometer 7a, and thus a lower rated value for this valve 4 is prescribed, then a lower concentration can be achieved. The further gas such as, for example, NO, should be diluted as much as possible in order to more easily regulate the flow-through quantity. Simultaneously, however, this dilution should still always be so small that the supply of the patient with oxygen is assured. Given higher flow-through quantities of the further gas, the oxygen flow or the oxygen concentration must be adapted under certain circumstances.

The regulation of the further valve 4 already carries out the setting of this concentration with adequate precision in and of itself. However, it provides no guarantee that this concentration is actually achieved. An error, for example in the control of this valve or of the further flow meter in this valve, can falsify the further gas flow, and thus the concentration, without a possibility of monitoring being normally established. Since the supplied quantity of nitrogen oxide and nitrogen gas is negligibly small in comparison to the respiratory gas, a monitoring of this supplied gas quantity is not possible via, for example, the measurement of the expirational gas flow.

The aggregate signal of the flow meters for the respiratory gas supply is connected onto the second potentiometer 7b of the double potentiometer 7a, 7b and is taken thereat in the same ratio as the rated value at the first potentiometer 7a. Furthermore, the output signal of the additional flow meter 6 is amplified by the same factor as is the signal of the further flow meter, by the factor 100 in the present case. This, however, means that the signal taken from the second potentiometer 7b, which thus is derived from the actual value of the respiratory gas flow, and the signal generated by the additional flow meter 6, should be of the same size after the amplification by the factor 100 when the system functions faultlessly. A deviation of these signals from one another indicates an error. In FIG. 1, both signals are forwarded via lines 10, 11 onto a monitoring arrangement 12 wherein a comparison of the two signals can be undertaken in the greatest variety of ways and, potentially, an alarm can be triggered. In addition, the concentration of the further gas can be identified and forwarded to a display 13. In the simplest case, the two signals can be directly compared to one another and a deviation beyond a prescribed value can be employed as a criterion for the triggering of an alarm. The output signal of the monitoring arrangement 12 can be employed via a further line 18 for the control of the valve 4 such that the valve 4 is closed, given the presence of a disturbance.

Advantageously, however, a monitoring as set forth in greater detail with reference to the following figures is proposed.

Figure 2:
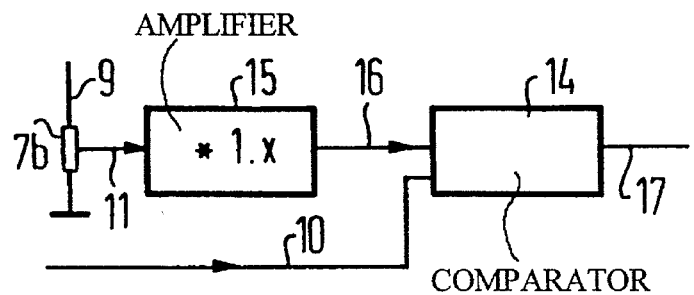
FIGS. 2 through 4 show three different embodiments of the signal treatment for generating an error signal.

FIG. 2 shows a first embodiment of the monitoring arrangement 12 as a block circuit diagram. It is essentially composed of a comparator 14 onto which the output signal of the additional flow meter 6 is connected via the line 10. The signal taken from the potentiometer 7b, which represents the rated value for the independent monitoring of the flow of the further gas, is first connected via the line 11 onto an amplifier 15 and is connected from the latter onto the comparator 14, as well as via the line 16. Given a correct flow regulation, the signals on the line 10 and, respectively, 11 are of the same size. In the amplifier 15, the rated value is slightly amplified by a factor 1.x, and thus a limit for the admissible fluctuation of the actual value for the flow of the further gas is set. When the actual value crosses this limit, then a signal that can be employed for triggering an alarm is generated on the output line 17 of the comparator.

The signal on the line 17 can also be possibly filtered, so that a disturbance is only indicated when the error signal appears over a defined time span.

Figure 3:
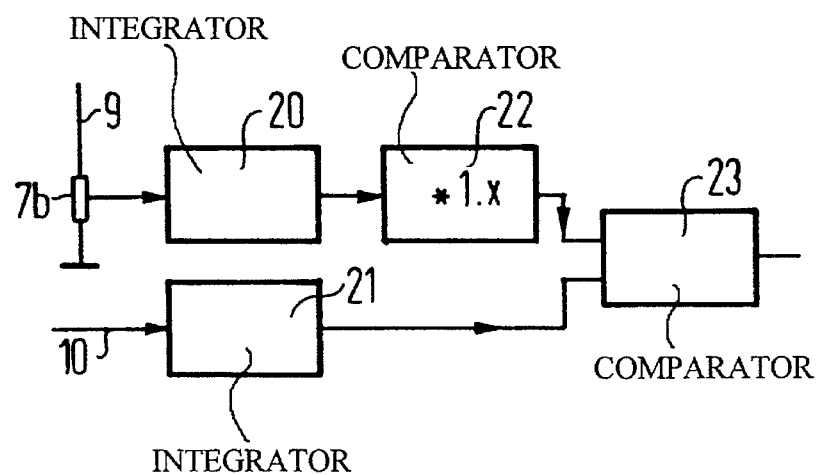

FIG. 3 shows an embodiment wherein the actual value and rated value are first connected onto integrators 20 or 21 before they are compared in a comparator 23 again via an amplifier 22 for the rated value. The integration, for example, can occur over a breath, or only over the inspiration phase. Chronological, slight shifts in the measurement of the gas flows that are produced by different placement of the flow meters and by the inertia of the gases in the lines can thus be averaged out in a simple way.

Figure 4:
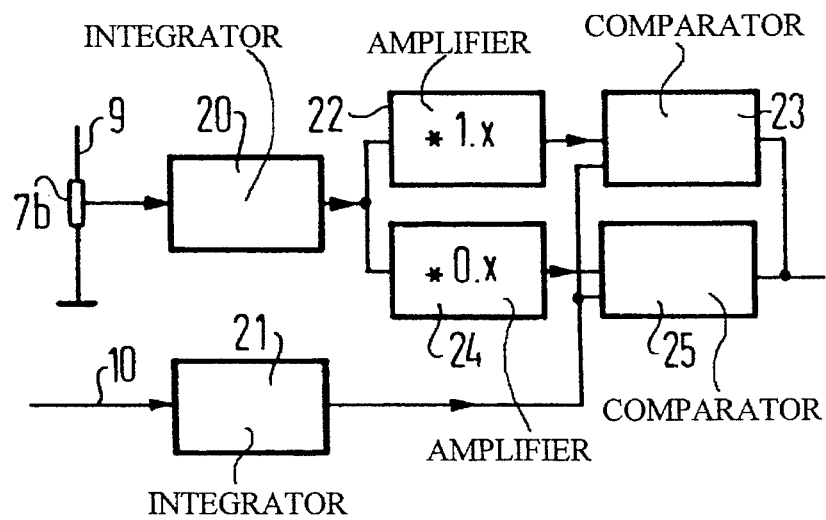

In the exemplary embodiment of FIG. 4, the value taken from the potentiometer 7b and integrated in the integrator is connected onto two amplifiers 22 and 24 that have different gains. The one amplifies, for example, by a factor 1.x and the other amplifies by the factor 0.x. As a result of this different amplification, an upper and a lower limit can thus be defined and a malfunction report occurs when the actual value upwardly or downwardly crosses them.

For this purpose, the output signals of the two amplifiers 22 and 24 are each respectively connected onto a comparator 23 or 25 onto which the output signal of the integrator 21 is likewise connected. The comparator 22 serves the purpose of comparison to the upper limit; the comparator 24 serves the purpose of comparison to the lower limit.

It is likewise possible within the framework of the invention to implement parts of the monitoring means in terms of software. Thus, for example, the signals on the lines 8, 9 and 10 in FIG. 1 can be digitized and supplied to a microprocessor that derives the rated value for the valve 4 therefrom and undertakes the independent monitoring of the further gas flow. The amplifiers, comparators and integrators can also be part of the microprocessor. Further, the concentrations for the respiratory gas and for the further gas, for example NO, can be calculated with the assistance of the microprocessor and be displayed via a display.

Although various minor changes and modifications might be suggested by those skilled in the art, it will be understood that we wish to include within the claims of the patent warranted hereon all such changes and modifications as reasonably come within our contribution to the art.

We claim as our invention:

1. An apparatus for independent monitoring of gas flow of a further gas delivered together with a respiratory gas to a respiratory path of a human or animal, said gas flow of said further gas being smaller than a gas flow of said respiratory gas, comprising:

a first flow meter means for measuring gas flow of the respiratory gas;

an additional flow meter means for measuring gas flow of the further gas;

a monitor means for comparing an output signal of said first flow meter means indicative of gas flow of the respiratory gas to an output signal from said additional flow meter means indicative of the measured gas flow of the respiratory gas, and for generating an error signal in response to said comparison;

a first controllable valve means associated with said first flow meter means for controlling gas flow of said respiratory gas, said first flow meter means output signal corresponding to actual quantity of respiratory gas flow;

a second controllable valve means for controlling delivery of said further gas to said respiratory path, said second controllable valve means having a second flow meter means for measuring the gas flow of said further gas;

said additional flow meter means being arranged between an output of said second valve means and a location at which the respective gas flows through the first and second valve means are united; and said monitoring means triggering an alarm given a deviation of the output signals of said additional flow meter means and said first flow meter means from one another beyond a prescribable value.

2. An apparatus for independent monitoring of gas flow of a further gas delivered together with a respiratory gas to a respiratory path of a human or animal, said gas flow of said further gas being smaller than a gas flow of said respiratory gas, comprising:

a first flow meter means for measuring gas flow of the respiratory gas;

an additional flow meter means for measuring gas flow of the further gas;

a monitor means for comparing an output signal of said first flow meter means indicative of gas flow of the respiratory gas to an output signal from said additional flow meter means indicative of the measured gas flow of the respiratory gas, and for generating an error signal in response to said comparison;

a first valve means regulating gas flow of said respiratory gas and a second valve means regulating gas flow of said further gas, and control means being provided for providing a first rated value for controlling said first valve means and a second rated value for controlling said second valve means where said second rated value is derived from the first rated value; and said control means comprising a first potentiometer having said first rated value connected thereto, a tap on said first potentiometer providing an output signal comprising said second rated value which is a portion of said first rated value.

3. An apparatus according to claim 2 wherein said control means further comprises a second potentiometer connected to said output signal of said first flow meter means, said second potentiometer having a tap at which a signal derived from said output signal of said first flow meter means is produced.

4. An apparatus according to claim 3 wherein the first and second potentiometers comprise a double potentiometer having a common drive for simultaneously adjusting taps of both the first and second potentiometers.

* * * * *